United States Patent
Lenchner et al.

(10) Patent No.: US 10,614,920 B2
(45) Date of Patent: *Apr. 7, 2020

(54) SYSTEM AND METHOD FOR COMPUTING SURVIVORSHIP RISK ASSOCIATED WITH DELAYING THERAPY IN BREAST CANCER

(71) Applicant: INTERNATIONAL BUSINESS MACHINES CORPORATION, Armonk, NY (US)

(72) Inventors: Jonathan Lenchner, Nairobi (KE); Charity Wayua, Nairobi (KE)

(73) Assignee: International Business Machines Corporation, Armonk, NY (US)

( * ) Notice: Subject to any disclaimer, the term of this patent is extended or adjusted under 35 U.S.C. 154(b) by 62 days.

This patent is subject to a terminal disclaimer.

(21) Appl. No.: 15/439,085

(22) Filed: Feb. 22, 2017

(65) Prior Publication Data
US 2018/0239875 A1 Aug. 23, 2018

(51) Int. Cl.
*G16H 50/20* (2018.01)
*G16H 50/30* (2018.01)
(Continued)

(52) U.S. Cl.
CPC .......... *G16H 50/20* (2018.01); *G06F 19/324* (2013.01); *G16H 10/40* (2018.01); *G16H 50/30* (2018.01)

(58) Field of Classification Search
None
See application file for complete search history.

(56) References Cited

U.S. PATENT DOCUMENTS

| 7,664,604 B1 * | 2/2010 | Heine | G16H 50/30 |
| | | | 702/19 |
| 2005/0282146 A1 * | 12/2005 | Kattan | G16H 50/20 |
| | | | 435/4 |

(Continued)

FOREIGN PATENT DOCUMENTS

WO    WO-2013093489 A2 *  11/2014  .............. C12Q 1/68

OTHER PUBLICATIONS

Tony H. H. Chen et al., Estimation of Sojourn Time in Chronic Disease Screening Without Data on Interval Cases, Biometrics 56, 167-172 (2000). (Year: 2000).*

(Continued)

*Primary Examiner* — Elaine Gort
*Assistant Examiner* — Nicholas Akogyeram, II
(74) *Attorney, Agent, or Firm* — Eyal Gilboa; Otterstedt, Wallace & Kammer, LLP

(57) ABSTRACT

An estimate is made of a time since a given presenting cancer would have first been detectable using a known diagnostic technique, and an estimate is also made of initial characteristics of the given presenting cancer at the time when it would have first been detectable using the known diagnostic technique. A first probability of the cancer being present in a first set of one or more clinically significant remote sites is determined based on the estimated initial characteristics. A second probability of the cancer being present in the first set of one or more clinically significant remote sites is determined based on actual current characteristics of the given presenting cancer. The first and second probabilities are used to estimate incremental risk of incurring presence of the cancer at the first set of one or more clinically significant remote sites by delaying therapy for a unit time.

20 Claims, 8 Drawing Sheets

(51) Int. Cl.

| | |
|---|---|
| *G16H 50/50* | (2018.01) |
| *G16H 50/70* | (2018.01) |
| *G16H 10/40* | (2018.01) |
| *G06F 19/00* | (2018.01) |
| *G01N 33/48* | (2006.01) |
| *G01N 33/50* | (2006.01) |
| *C12Q 1/6886* | (2018.01) |

(56) References Cited

U.S. PATENT DOCUMENTS

2015/0112705 A1* 4/2015 Neville .................. G06F 19/00 705/2
2019/0180849 A1* 6/2019 Hagar ...................... A61B 5/02

OTHER PUBLICATIONS

A.S. Gur et al., Validation of breast cancer nomograms for predicting the non-sentinel lymph node metastases after a positive sentinel lymph node biopsy in a multi-center study, European Journal of Surgical Oncology 36, 30-35 (2010). (Year: 2009).*

Racquel Cobos Campos et al., Clinical impact of delaying initiation of radiotherapy in patients with breast cancer: stages 0, I and II, a retrospective observational study, Journal of Radiotherapy in Practice 244-251 (2015). (Year: 2015).*

Michelle C. Specht et al., Predicting Nonsentinel Node Status After Positive Sentinel Lymph Biopsy for Breast Cancer: Clinicians Versus Nomogram. Annals of Surgical Oncology, 12(8): pp. 654-659. Jun. 2005.

American Cancer Society, Breast Cancer Prevention and Early Detection. 2015, pp. 1-23.

American Cancer Society, Mammograms and Other Breast Imaging Tests. 2014, pp. 1-26.

Memorial Sloan Kettering Cancer Center, Breast Cancer Nomogram: Breast Additional Non SLN Metastases. Downloaded from http://nomograms.mskcc.org/breast/BreastAdditionalNonSLNMetastasesPage.aspx on Dec. 21, 2016. pp. 1-4.

Memorial Sloan Kettering Cancer Center, Breast Cancer Nomogram: Sentinel Lymph Node Metastasis. http://nomograms.mskcc.org/breast/BreastSLNodeMetastasisPage.aspx on Dec. 21, 2016. pp. 1-4.

Peter Mell and Timothy Grance, NIST, The NIST Definition of Cloud Computing. Special Publication 800-145, Sep. 2011. pp. 1-7.

José Luiz B. Bevilacqua et al, Doctor, What Are My Chances of Having a Positive Sentinel Node? A Validated Nomogram for Risk Estimation. Journal of Clinical Oncology, vol. 25, # 24, Aug. 20, 2007. pp. 3670-3679.

Nomogram. Downloaded from https://en.wikipedia.org/wiki/Nomogram on Dec. 7, 2016. pp. 1-7.

Kimberly J. Van Zee et al, A Nomogram for Predicting the Likelihood of Additional Nodal Metastases in Breast Cancer Patients With a Positive Sentinel Node Biopsy. Annals of Surgical Oncology, vol. 10 #10, pp. 1140-1151, 2003.

Isabelle Soerjomataram et al, An overview of prognostic factors for long-term survivors of breast cancer. Breast Cancer Res Treat (2008) 107. pp. 309-330.

A. Castellino, "Time is of the essence in breast cancer: Don't Delay". Medscape Online, Dec. 10, 2015. pp. 1-4.

A. Walks, T. King and E. Winer, "Timeliness in breast cancer treatment—the sooner the better," JAMA Oncology 2(3): 302-304. Mar. 2016.

M. Chavez-MacGregor, C. Clarke, D. Lichtensztajn and S. Giordano, "Delayed initiation of adjuvant chemotherapy among patients with breast cancer," JAMA Oncology 2(3): 322-329. 2016 published on-line Dec. 10, 2015.

R. J. Bleicher et al., "Time to surgery and breast cancer survival in the United States," JAMA Oncology 2(3): 330-339. 2016, published on-line Dec. 10, 2015.

P. McAuliffe, S. Danoff, S. Shapiro, and N. Davidson, "Treatment for breast cancer: is time really of the essence?," Journal of the National Cancer Institute, 105(2): 80-82. 2012.

R. J. Bleicher et al., "Preoperative delays in the US Medicare population with breast cancer," Journal of Clinical Oncology, 30(36):4485-4492, 2012.

Jonathan Lenchner, et al., unpublished U.S. Appl. No. 15/859,348, filed Dec. 30, 2017, System and Method for Computing Survivorship Risk Associated With Delaying Therapy in Breast Cancer, pp. 1-38 plus 8 sheets of drawings.

Paul J. Otterstedt, List of IBM Patents or Patent Applications Treated as Related, Jun. 19, 2018, pp. 1-2.

* cited by examiner

| Probabilities obtained from Nomograms |
|---|
| $p_{0,s+}$ = probability of one or more nodes involved at earliest possible detection (= probability of sentinel node involvement at earliest possible detection); previously denoted $p_0$: probability obtained from 1st nomogram. |
| $p_{0,a|s+}$ = probability of additional nodal involvement given sentinel node involvement at earliest possible detection: probability obtained from 2nd nomogram. |
| $p_{s+}$ = probability of one or more nodes involved currently (= probability of sentinel node involvement currently); previously denoted p: probability obtained from 1st nomogram. |
| $p_{a|s+}$ = probability of additional nodal involvement given sentinel node involvement currently: probability obtained from 2nd nomogram. |

*FIG. 5*

| Probabilities Needed |
| --- |
| $p_{0,s}$ = probability of just sentinel node involvement at earliest possible detection. |
| $p_{0,a}$ = probability of additional nodal involvement at earliest possible detection. |
| $p_s$ = probability of just sentinel node involvement currently. |
| $p_a$ = probability of additional nodal involvement currently. |

FIG. 6

| How to Compute Needed Probabilities from those Obtained from Nomograms |
| --- |
| $p_{0,a} = p_{0,s+} * p_{0,a|s+}$ |
| $p_{0,s} = p_{0,s+} - p_{0,a}$ |
| $p_a = p_{s+} * p_{a|s+}$ |
| $p_s = p_{s+} - p_a$ |

FIG. 7

SYSTEM AND METHOD FOR COMPUTING SURVIVORSHIP RISK ASSOCIATED WITH DELAYING THERAPY IN BREAST CANCER

BACKGROUND

The present invention relates to medical analytics, and more specifically, to medical analytics as related to assessing cancer survivorship risk.

Upon a diagnosis of breast cancer, especially when the tumor or tumors are nonpalpable or small, surgeons, oncologists, and nurses often tell the patient that putting off therapy (e.g., surgery or chemotherapy) by a month or two does not have an appreciable impact on long-term survival. As noted in R. J. Bleicher et al., "Preoperative delays in the US Medicare population with breast cancer," Journal of Clinical Oncology, 30(36):4485-4492, 2012, expressly incorporated herein by reference in its entirety for all purposes, the time from diagnosis of breast cancer to initiation of therapy has risen steadily over the last 20 years. However, recent studies suggest that putting off therapy does in fact reduce a patient's survival probability. Accordingly, it is desirable to provide an estimate of the risk associated with delaying therapy when given presenting cancer characteristics and other variables, such as, for example, size of tumor, protein receptor status, single or multi-focality, and age of patient.

SUMMARY

Principles of the invention provide techniques for a system and method for computing survivorship risk associated with delaying therapy in breast cancer. In one aspect, an exemplary method includes the steps of estimating a time since a given presenting cancer would have first been detectable using a known diagnostic technique; estimating initial characteristics of the given presenting cancer at the time when it would have first been detectable using the known diagnostic technique; determining first probability of the cancer being present in a first set of one or more clinically significant remote sites based on the estimated initial characteristics; determining second probability of the cancer being present in the first set of one or more clinically significant remote sites based on actual current characteristics of the given presenting cancer; and using the first and second probabilities to estimate incremental risk of incurring presence of the cancer at the first set of one or more clinically significant remote sites by delaying therapy for a unit time.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments provide one or more of:

Computing an incremental decrease in survival probability due to delaying treatment of breast cancer, where the computation is easily updated by accessing current databases and nomograms;

Estimating the increased probability of requiring chemotherapy following surgery as a result of delaying surgery;

Estimating the increased probability of requiring radiation following surgery as a result of delaying surgery;

Facilitating the optimal use of medical personnel and facilities, so that those with the greatest risk associated with delaying treatment get treated first.

These and other features and advantages of the present invention will become apparent from the following detailed description of illustrative embodiments thereof, which is to be read in connection with the accompanying drawings.

BRIEF DESCRIPTION OF THE DRAWINGS

FIGS. 5-7 provide tables of, respectively, obtained probabilities, desired probabilities, and techniques for calculating probabilities according to an embodiment of the present invention;

DETAILED DESCRIPTION

Figure 1:
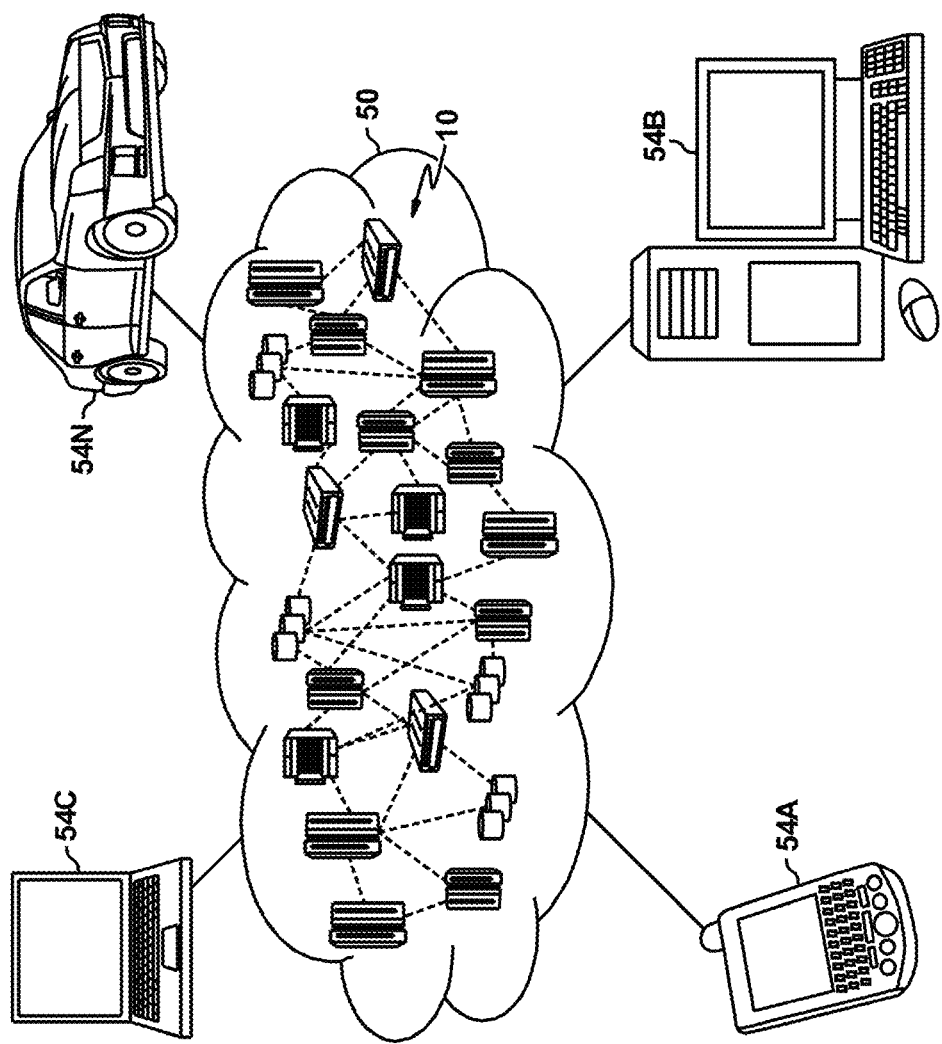
FIG. 1 depicts a cloud computing environment according to an embodiment of the present invention.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
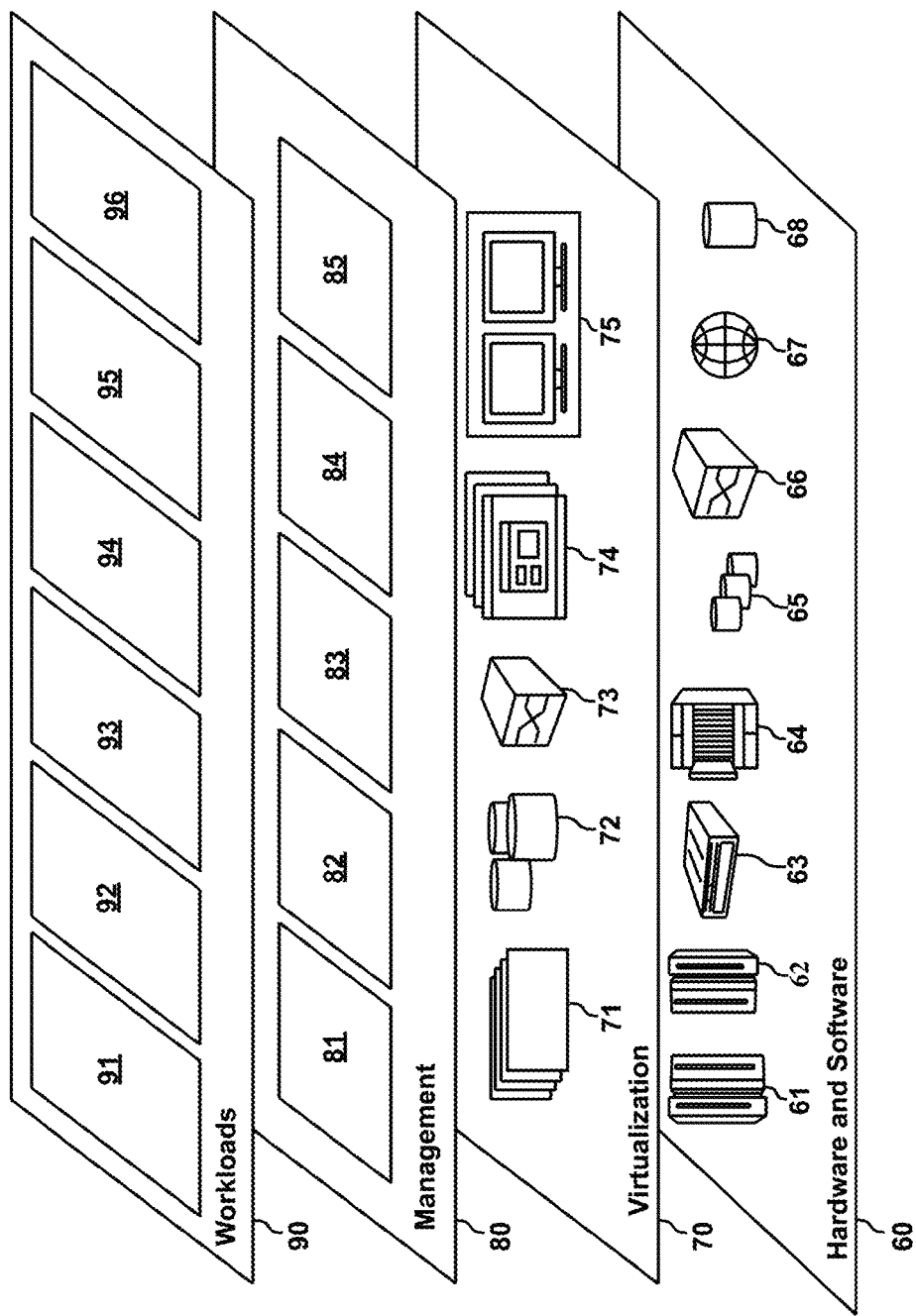
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a workload 96 to provide access to databases and nomograms to facilitate the computation of survivorship risk associated with delaying therapy for breast cancer. For example, the workload 96 may provide an API (Application Programming Interface) to obtain incremental survivorship risk associated with a given delay in treatment as well the incremental risk of needing radiation or chemotherapy after surgery.

Embodiments provide for the computation of an incremental decrease in survival probability per unit time in delaying breast cancer therapy. Embodiments access and make use of available databases and nomograms that provide survival probabilities, and probabilities associated with lymph node involvement. Accordingly, databases and nomograms, although not designed to yield the incremental decrease in survival probability per unit time in delaying breast cancer therapy, can nevertheless be used in an embodiment in deriving such incremental decrease in survival probability. Providing such information to a patient may be useful in their understanding of the risks involved in delaying therapy once breast cancer has been diagnosed. Such information may also be useful to an oncology facility to help them most efficiently allocate resources.

Historically a nomogram was a two-dimensional diagram designed to allow the approximate graphical computation of a mathematical function of n variables using a parallel coordinate system, rather than standard Cartesian coordinates. Such nomograms consisted of a set of n+1 scales, one for each variable in an equation. Knowing the values of n variables, the value of the unknown variable could be found. Laying a straightedge across the known values on the scales and reading the unknown value from where the straightedge crossed the scale for that variable one obtained the result. Not all continuous scalar functions of n variables can be represented using such a nomogram. One or more embodiments disclosed herein allow for more general nomograms. As used herein, a nomogram is any tool, typically one that employs a graphical user interface, that is used to calculate the approximate probability of some outcome (e.g. cancer metastasis of a particular sort), given the values of a given set of n variables (e.g. presenting characteristics of a given cancer and various demographic characteristics of the patient). In a non-limiting example, the number of variables n may be quite high (e.g., ten).

Nomograms are readily available through well-known medical websites. For example, the Memorial Sloan Kettering (MSK) Cancer Center provides nomograms on their website. As specific examples, a nomogram for estimating the probability of sentinel lymph node metastasis given a presenting instance of breast cancer may be found at the following URL (space dot space substituted for "." to avoid inclusion of browser-executable code), the contents of which are expressly incorporated by reference herein in their entirety for all purposes: http://nomograms dot mskcc dot org/breast/BreastSLNodeMetastasisPage dot aspx (see also Jose Luiz B. Bevilacqua et al., "Doctor, What Are My Chances of Having a Positive Sentinel Node? A Validated Nomogram for Risk Estimation," J. Clinical Oncology VOLUME 25 NUMBER 24 Aug. 20, 2007, pages 3670-3679, also expressly incorporated by reference herein its entirety for all purposes) and a nomogram for estimating the probability of additional, non-sentinel lymph node metastasis given a sentinel node metastasis may be found at the following URL (space dot space substituted for "." to avoid inclusion of browser-executable code), the contents of which are expressly incorporated by reference herein in their entirety for all purposes: http://nomograms dot mskcc dot org/breast/BreastAdditionalNonSLNMetastasesPage dot aspx (see also Michelle C. Specht et al., "Predicting Non-sentinel Node Status After Positive Sentinel Lymph Biopsy for Breast Cancer: Clinicians Versus Nomogram," Annals of Surgical Oncology, 12(8): 654-659, Jun. 16, 2005, expressly incorporated by reference herein its entirety for all purposes, and Kimberly J. Van Zee et al., "A Nomogram for Predicting the Likelihood of Additional Nodal Metastases in Breast Cancer Patients With a Positive Sentinel Node Biopsy," Annals of Surgical Oncology, 10(10):1140-1151, 2003, also expressly incorporated by reference herein its entirety for all purposes).

To describe exemplary embodiments, suppose a patient has undergone a mammogram for which there is an indication of breast cancer. Embodiments typically first use a suitable nomogram to determine risk (e.g. of spread to the sentinel node) at the present time and then try to estimate when the cancer would first have been detectable via mammogram, what its characteristics were at that time, and what the nomogram-predicted risk (e.g. of spread to the sentinel node) would have been based on those estimated characteristics (in essence, back-dating the breast cancer to a likely first possible mammogram detection). Alternatively stated, embodiments estimate a time duration D since a first possible mammogram detection. It is to be understood that the first possible mammogram detection is not an actual mammogram detection, but rather represents an estimate of when the breast cancer may have been first detected by a mammogram.

As a specific example, suppose a patient is presented to a medical practitioner in which there is a mammogram detection of breast cancer, providing a set of presented cancer characteristics, where the patient previously had a mammogram 14 months ago but without breast cancer detection at that time. A relatively simple method of back-dating that can be used in the absence of additional information is to take the time since the previous mammogram and to halve that number, which in this particular example would be 7 months. Accordingly, the first possible mammogram detection is estimated to have been 7 months prior to the current mammogram, and therefore the time duration D since a first possible mammogram detection is 7 months. Embodiments then estimate the cancer characteristics associated with the first possible mammogram detection. Accordingly, embodiments estimate a time at which a first possible mammogram detection could have occurred and a set of cancer characteristics associated with the first possible mammogram detection.

Consider a first type of nomogram that in response to inputting a set of patient demographic characteristics and a set of cancer characteristics outputs the probability of a positive sentinel lymph node biopsy. Embodiments input into the nomogram the set of estimated characteristics associated with the first possible mammogram detection, along with the set of patient demographic characteristics. The output (result) of the nomogram is a probability $q_s$ of a positive sentinel node biopsy result for the first possible mammogram detection. It is to be understood that the probability $q_s$ is an estimate of the probability of a positive sentinel node because an estimate was made for the time at which a mammogram (the "first possible mammogram"), if performed, may have likely yielded cancer detection.

Embodiments also use the first type of nomogram again, but input the set of presented cancer characteristics along with the set of patient demographic characteristics. The result of the nomogram is a probability $p_s$ of a positive sentinel lymph node biopsy for the present mammogram detection.

Embodiments interpolate the probabilities $p_s$ and $q_s$ over the time duration D to estimate an incremental survival risk per unit time in delaying therapy. In one embodiment, this interpolation is a simple linear interpolation, $(p_s - q_s)/D$.

In an embodiment, medical literature or databases are accessed to provide a survival probability associated with the set of presented cancer characteristics for the case of node involvement, denoted as $S_+$, and for the case of no node involvement, denoted as $S_-$. These survival probabilities are for some given number of years. For example, the five-year survival probabilities may be obtained for the cases of node involvement and no node involvement, or as another example the ten-year survival probabilities may be obtained.

In an embodiment, the incremental decrease in survival probability per unit time in delaying therapy in terms of the above-described quantities is given by $$(S_+ S_-)(p_s - q_s)/D.$$

As a specific example of the above-described embodiment, suppose a 55 year old female patient presents with an HER2-positive (Human Epidermal Growth Factor Receptor 2), ER-negative (Estrogen Receptor), PR-negative (Progesterone Receptor) breast cancer with three distinct sites in the same (left) breast, where the sites are 1 cm, 0.8 cm, and a 0.5 cm microcalcification site (e.g. an instance of ductal carcinoma in situ, DCIS). All sites are nonpalpable. Using the same example above in which the patient last had a mammogram 14 months ago, the time duration D is 7 months.

As an example of providing a set of estimated cancer characteristics, most likely in this case the cancer would have been first detectable as a small microcalcification (ductal carcinoma in situ) cluster with a size of about 0.5 cm.

Entering the above estimated quantities for the first possible mammogram detection into the first type of nomogram, as provided by the Memorial Sloan Kettering Cancer Center, yields a probability $q_s$ of 0.07. Entering the set of presented cancer characteristics into the first type of nomogram yields a probably $p_s$ of 0.27. Thus, over the estimated 7 months there has been an increased likelihood of sentinel node involvement of 0.20, and accordingly the increased likelihood of such node involvement given a month's delay in therapy is approximately 0.20/7=0.0286.

An embodiment then accesses the medical literature or appropriate medical databases to obtain survival probabilities, for example the ten-year survival probabilities with and without node involvement. Referring to "An Overview Of Prognostic Factors For Long-Term Survivors Of Breast Cancer," I. Soerjomataram, M. W. J. Louwman, J. G. Ribot, et al., Breast Cancer Res Treat (2008) 107: 309 doi:10.1007/s10549-007-9556-1, expressly incorporated herein by reference in its entirety for all purposes, for the above set of presented cancer characteristics and the set of patient characteristics, the survival probability without node involvement $S_-$ is 0.84 and the survival probability with node involvement $S_+$ is 0.50. As a result, the incremental decrease in survival probability due to a one month delay in therapy is approximately (0.84−0.50)(0.0286)=0.0097, or about 1%.

The Soerjomataram et al. paper is one example of a resource for obtaining survival probabilities. Embodiments may access many other research papers and databases to obtain such information.

Figure 3:
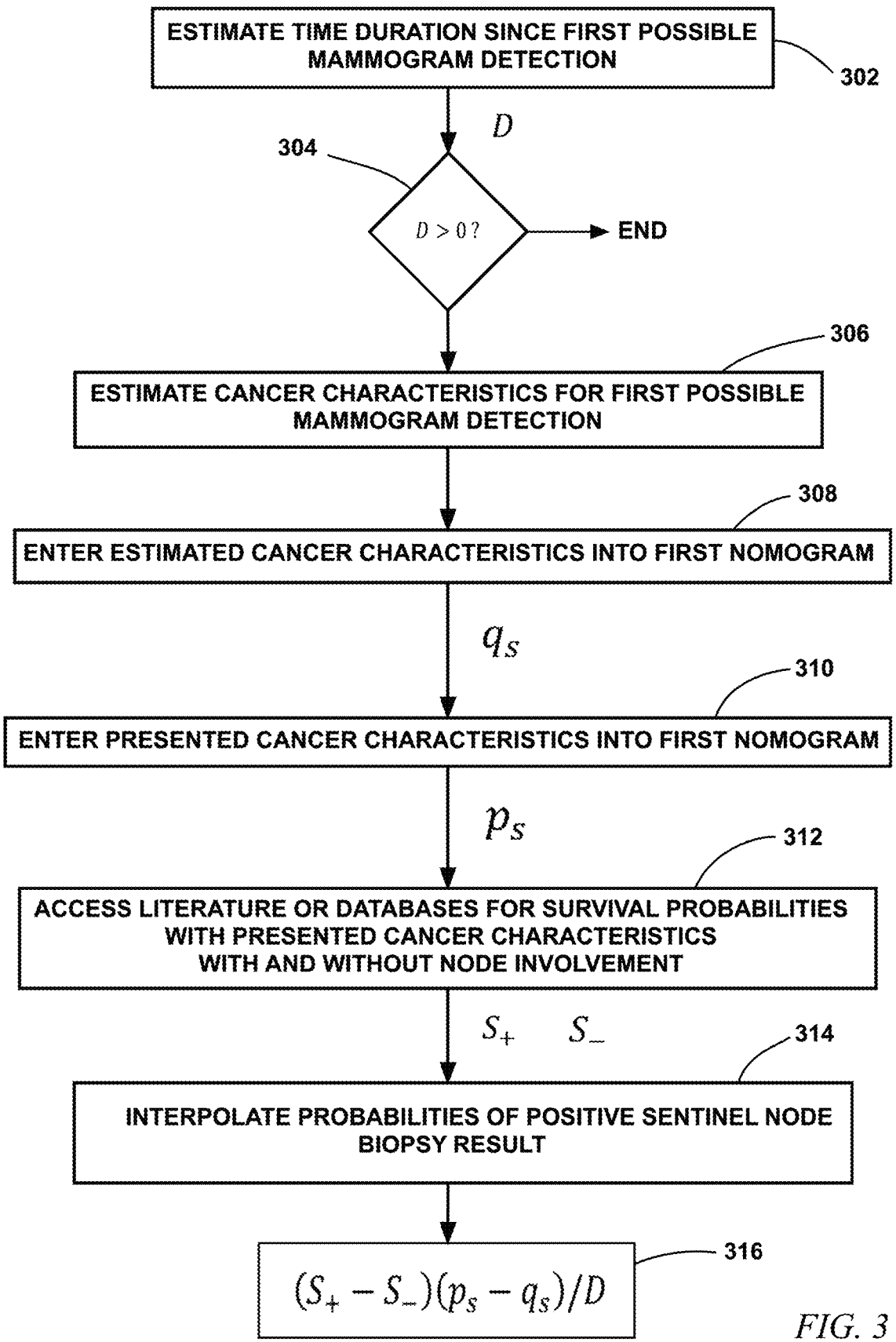
FIG. 3 illustrates a flow diagram according to an embodiment of the present invention.

FIG. 3 illustrates a flow diagram for the above-described embodiment. Given a patient with a set of presented cancer characteristics, in step 302 an estimate is made for the time duration D since a first possible mammogram detection. Assuming that such a time duration can be estimated, as indicated by the decision 304, in step 306 an estimate is made of the cancer characteristics associated with the first possible mammogram detection. In step 308, the set of estimated cancer characteristics, along with the set of patient demographic characteristics, is entered into a first type of nomogram to provide a first probability of a positive sentinel lymph node biopsy for the patient, $q_s$. In step 310, the set of presented cancer characteristics, along with the set of patient demographic characteristics, are entered into the first type of nomogram to provide a second probability of positive sentinel node biopsy result for the patient, $p_s$.

The first type of nomogram could be stored locally on a computing device available to the medical practitioner, or it may be made available as a cloud computing service, where an application on a locally available computing device, such as a smartphone, interacts with a remote server providing the cloud computing service.

In step 312, medical literature or databases are accessed to provide the survival probabilities, $S_+$ and $S_-$, associated with the set of presented cancer characteristics and the set of patient characteristics, for the case with and without sentinel lymph node involvement, respectively. In step 314, an interpolation is applied to the first and second probabilities of a positive sentinel node biopsy result over the time duration D to estimate an incremental increase in risk of sentinel lymph node metastasis per unit time in delaying therapy, and this result is used in step 316 to provide an incremental decrease in survival probability per unit time in delaying therapy. In the particular embodiments represented by FIG. 3, the interpolation carried out in step 314 is the simple linear interpolation $(p_s - q_s)/D$, and the incremental decrease an survival probability per unit time in delaying therapy in step 316 is given by $(S_+ - S_-)(p_s - q_s)/D$, as discussed previously.

A resource such a remote server or cloud service, such as for example the workload 96, may be accessed to provide the medical literature or databases from which the survival probabilities, $S_+$ and $S_-$, are obtained. Such content could be stored locally on a computing device readily available to the medical practitioner, but the content may need to be updated as survival rates change, whereas a cloud service could be structured to provide current information relevant to survival probabilities in a completely transparent manner to the medical practitioner.

Figure 4:
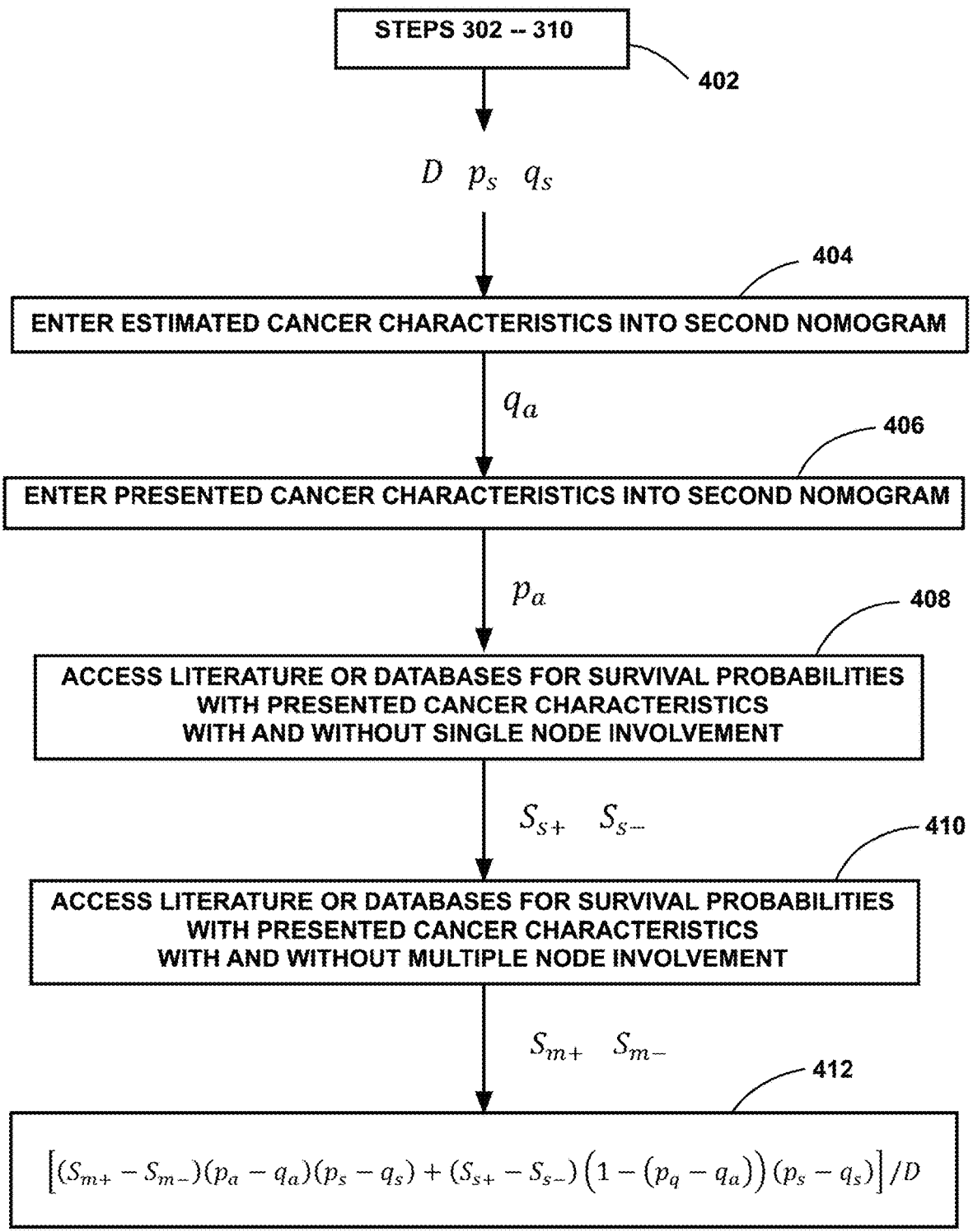
FIG. 4 illustrates a flow diagram according to another embodiment of the present invention.

FIG. 4 illustrates a flow diagram according to another embodiment, which may be viewed as a refinement to the previously described embodiments, e.g., FIG. 3, in that additional information is accessed. Referring to FIG. 4, in step 402 the steps 302 through 310 as described with respect to FIG. 3 are performed to yield the time duration D, the probability $p_s$ of a positive sentinel node biopsy result for the set of presented cancer characteristics associated with the present mammogram detection, and the probability $q_s$ of a positive sentinel node biopsy result for the set of estimated cancer characteristics associated with the first possible mammogram detection.

Accessing a first type of nomogram provides the probabilities $p_s$ and $q_s$. In steps 404 and 406, a second type of nomogram is accessed to provide conditional probabilities. The second type of nomogram, in response to inputting a set of cancer characteristics and a set of patient demographic characteristics, outputs a conditional probability of additional non-sentinel lymph node involvement conditioned on a positive sentinel node biopsy result. As for the first type of nomogram, the second type of nomogram may be found at the web site of the Memorial Sloan Kettering Cancer Center.

In step 404, the set of estimated cancer characteristics associated with the first possible mammogram detection, and the set of patient demographic characteristics, are provided as input to the second type of nomogram. The second nomogram provides as output a conditional probability, denoted by $q_a$ of additional, non-sentinel lymph node involvement at the first possible mammogram detection. In step 406, the set of presented cancer characteristics associated with the present mammogram, and the set of patient characteristics, are provided as input to the second type of nomogram. With this input, the second type of nomogram outputs a conditional probability, denoted by $p_a$, of additional, non-sentinel lymph node involvement at the present time.

In steps 408 and 410, medical literature or databases are accessed to provide survival probabilities for the set of presented cancer characteristics and the set of patient demographic characteristics. Step 408 provides a survival probability $S_{s+}$ with sentinel node involvement and a survival probability $S_{s-}$ without sentinel node involvement. Step 410 provides a survival probability $S_{m+}$ with sentinel and axillary node involvement and a survival probability $S_{m-}$ with sentinel node involvement but without axillary node involvement. In step 412, an incremental decrease in survival probability per unit time in delaying therapy is computed as $$[(S_{m+}-S_{m-})(p_a-q_a)(p_s-q_s)+(s_{s+}-s_{s-})(1-(p_q-q_a))(p_s-q_s)]/D.$$

As discussed with respect to the embodiment of FIG. 3, the medical literature or database accessed to provide the survival probabilities with respect to the embodiment of FIG. 4 may be provided by way of a cloud service so as to be current. However, such content may be stored in a computing device local to the medical practitioner.

Recapitulation and Specific Example

One or more embodiments provide a risk assessment tool using one or both of the above-mentioned MSK nomograms to back into an estimate of the increased risk of delaying treatment by a given increment of time following initial diagnosis. A first, short, or simple method uses the MSK nomogram for assessing the probability of sentinel lymph node involvement. A second, longer, more sophisticated technique uses both this first MSK nomogram as well as the MSK nomogram for assessing additional nodal involvement. In conjunction with the nomograms, the above-mentioned comprehensive 2008 Soerjomataram study is employed, which assesses the 10-year mortality-based hazard ratios associated with various prognostic factors. In this non-limiting specific detailed embodiment, the interest is the hazard ratios associated with primary and axillary lymph node involvement.

Given a patient with a presenting case of breast cancer, the first step in assessing the patient's risk associated with delaying therapy is to fill in the patient's tumor and demographic information in the MSK nomogram for assessing the probability of sentinel node involvement. Consider the illustrative case of a 56 year-old patient with multi-focal HER2+ breast cancer. The patient presented with a tumor of size 1.2 cm, another of size 1.0 cm, and a third, slightly smaller site of DCIS (ductal carcinoma in situ). In a non-limiting example, the user is prompted to enter the patient's current age (e.g. from 20 to 91); here, 56. The user is further prompted to enter the size of the primary breast tumor as measured in an imaging study or pathological exam, from 0.1 cm to 11.0 cm); here, 1.2 cm. Next, the user is queried as to whether the tumor is of a special type; in particular, to indicate if the tumor has been pathologically defined as pure tubular, pure colloid (mucinous), or typical medullary carcinomas on the pathology report. The user may also receive an indication that other histologies such as atypical medullary carcinoma with ductal and lobular features should be classified as ductal and may be referred to a separate tumor type and grade section.

The user may be queried whether the tumor is confined within the upper inner quadrant (UIQ) of the breast, whether there is lymphatic or vascular structure involvement, and whether there are cells separated from the main tumor mass (multifocality). The user may be further presented with a list of tumor types and grades from which the tumor type and grade of the individual can be selected. The user may be prompted to indicate whether the tumor type is ductal or lobular as per the pathology report. If ductal, the user may be prompted to indicate the nuclear grade, viz., (I) slight or no variation in nucleus size, (II) moderate variation in size and shape of nucleus, or (III) marked variation in size and shape of nucleus.

Further prompts may inquire as to estrogen receptor status; e.g., negative if estrogen receptors stain positive in less than ten percent of cells, otherwise positive; and progesterone receptor status; e.g., negative if progesterone receptors stain positive in less than ten percent of cells, otherwise positive.

In the non-limiting example, the data entered may include age 56; tumor size 1.2 cm; negative for special tumor type and tumor confined to UIQ; yes for lymphatic or vascular structure involvement; yes for multifocality; Ductal, II for tumor type and grade; and negative for estrogen receptor status and progesterone receptor status.

After filling out the nomogram, use it to calculate the probability of sentinel node involvement, obtaining a probability denoted by p. In the case of the exemplary patient data, p=0.56. Then, make note of the number of months since the patient has been in for her last mammogram and call this duration D. In this case, the patient's last mammogram was 14 months earlier so D=14 months. Next, try to "roll back the camera" to the earliest time the existing cancer might have been detectable under mammography. What would the original presentation have been like? In the case of the exemplary patient, estimate the initial presentation to have been a single 0.5 cm instance of DCIS with no lymphatic or vascular structure involvement. Complete the nomogram with those estimated past characteristics instead of the actual current characteristics, given the estimated answers to the questions set forth just above. In the non-limiting example, the data entered for the estimated past characteristics may include age 56; tumor size 0.5 cm; negative for special tumor type and tumor confined to UIQ; negative for lymphatic or vascular structure involvement; negative for multifocality; Ductal, I for tumor type and grade; and negative for estrogen receptor status and progesterone receptor status. Again calculate the probability of sentinel node involvement, obtaining a probability denoted by $p_0$. In the case of the illustrative patient, $p_0$=0.07. Now, take the value of D=14 months since the last mammogram and make the naive estimate that the first visible lesion would have manifested itself at a point D/2=7 months earlier. Thus, over the estimated 7 months, the patient has incurred an additional likelihood of sentinel node involvement of $p-p_0$=0.49, and, extrapolating linearly, waiting an additional month will incur an incremental risk of approximately $(p-p_0)/(D/2)$=0.49/7=0.07. Note that this linear addition of incremental risk cannot continue forever, since the risk of sentinel node involvement cannot exceed 1 and the delay vs. risk curve is almost certainly sigmoid; however, for values of p below about 0.75 the linearity assumption is believed to be reasonably conservative.

Next refer to Soerjomataram et al. to obtain the hazard ratio for 10 year survival associated with sentinel lymph node involvement—the hazard ratio in this case being 2.4. A values of 0.07 of this hazard ratio is incurred in an incremental month, i.e. 0.07*(2.4−1.0)=0.098, so that the hazard ratio associated with waiting an additional month is approximately 1.098, or in this case, a value that is very similar to the aggregate value obtained in R. J. Bleicher et al., "Time to surgery and breast cancer survival in the United States,' JAMA Oncology, 2(3):330-339, 2016, expressly incorporated herein by reference in its entirety for all purposes, when studying patients of all different tumor presentations and demographic characteristics. In general for values of p, $p_0$ and D, the approximate incremental hazard ratio of waiting an additional month, $HR_{inc-month}$, is $$HR_{inc-month}=1+2.8(p-p_0)/D \qquad (1)$$

or for a generic reporting of hazard ratio associated with sentinel node involvement, $HR_{sent-node}$, $$HR_{inc-month}=1+2(p-p_0)(HR_{sent-node}-1) \qquad (2)$$

For extra precision, both the sentinel lymph node nomogram and the additional lymph node nomogram can be used. In this case, fill out the MSK additional lymph node nomogram. The first question may include whether a frozen section was performed. A frozen section, though expeditious, is not the most reliable method of assessing a positive sentinel node. Since this embodiment conditions probabilistic estimates on a 100% confident sentinel node determination, answer NO to the Frozen Section Performed question in the nomogram. A second question can include the pathological size of the primary tumor, in centimeters (e.g., 0.1 to 9.0 cm). A third question may refer to the tumor type and grade, as discussed above. A fourth question may refer to the number of sentinel lymph nodes found to have cancer when biopsied (e.g., 1 to 7), while a fifth question may refer to the method used to determine that cancer had spread to the sentinel lymph nodes (e.g., routine H & E—Hematoxylin and eosin stain). A sixth question may refer to the number of sentinel lymph nodes found not to have cancer when biopsied (e.g., 0 to 14). A seventh question may refer to lymphatic or vascular structure involvement, as discussed above; an eighth question may refer to multifocality, as discussed above; and a ninth question may refer to whether the breast cancer cells tested positive for estrogen receptors.

The only determination provided, given the 100% conditioning, is that of a single positive sentinel node, hence the answers to the fourth and sixth questions as one and zero respectively. Answers to the remaining questions are consistent with the answers given in the earlier nomogram. In sum, answers can include negative for frozen section performed; 1.2 cm for tumor size; Ductal, II for tumor type and grade; 1 positive sentinel node; detection by routine H & E; 0 negative sentinel nodes; affirmative for lymphatic or vascular structure involvement and multifocality; and negative for estrogen receptor positive. If the probability of additional lymph node involvement is now calculated, obtain the conditional probability of additional lymph node involvement given sentinel node involvement. This probability is denoted by $p_0$. In the case of the data just mentioned, the nomogram returns $p_{a|s}$=0.50, though the computation will now be carried out using $p_{a|s}$. For axillary node involvement, the 2008 Soerjomataram study is not detailed enough to enable a crisp additional estimate, saying only that "Prognosis for patients with 10 or more involved axillary nodes showed 70% more deaths at 10 years than for those with 1-3 involved nodes." Thus, results in this exemplary case are stated in terms of values that may become available upon a detailed analysis of the SEER-Medicare and U.S. National Cancer datasets used in R. J. Bleicher et al., "Time to surgery and breast cancer survival in the United States,' JAMA Oncology, 2(3):330-339, 2016.

To arrive at an appropriate formula for just sentinel node involvement, some additional notation is introduced in the tables of FIGS. 5, 6, and 7. Then, if it is possible to obtain the hazard ratio, $HR_{sent-only}$, associated with only having sentinel lymph node involvement and no others, together with the hazard ratio, $HR_{additional}$, associated with having additional lymph node involvement, obtain:

$$HR_{inc-month}=1+2(p_s-p_{0,s})(HR_{sent-only}-1)/D+2(p_a-p_{0,a})(HR_{additional}-1)/D \qquad (3)$$

or $$HR_{inc-month}=1+(2/D)[(p_s-p_{0,s})(HR_{sent-only}-1)+(p_a-p_{0,a})(HR_{additional}-1)] \qquad (4)$$

One or more embodiments thus provide estimates for approximating the risk of delaying treatment following initial diagnosis of cancers such as breast cancer. These estimates use estimates of when a first possible diagnosis (e.g. via mammogram) might have been possible. Further, the risk of nodal involvement is approximated as increasing linearly from this hypothetical first possible diagnosis, a supposition that does not hold, even approximately, beyond a certain number of months, and not for breast cancers which have not been caught early and for which the probability of nodal involvement may already be approaching 1. In the case of p near 1 an explicit sigmoid assumption about the shape of the delay vs. risk curve can be made in some instances, in which case the preponderance of the risk may shift to that of incurring axillary node involvement as assessed by the second nomogram. Additionally, one or more embodiments do not apply to the case when a tumor is caught (e.g. on mammogram) as early as conceivably possible (i.e. for D=0).

It is possible to add informal error bars to the estimates, e.g. by supposing that the first detectable mammogram was anywhere say from 1 month prior (greatest risk of delay), to D−1 months prior (least risk of delay), where, again, D denotes the time since the patient's last mammogram or similar diagnostic procedure.

Given the discussion thus far, it will be appreciated that, in general terms, an exemplary method, according to an aspect of the invention, includes the step of estimating a time since a given presenting cancer would have first been detectable using a known diagnostic technique. In a non-limiting example, simply take half the time since the last (negative) diagnostic procedure (e.g., mammogram). A further step includes estimating initial characteristics of the given presenting cancer at the time when it would have first been detectable using the known diagnostic technique. This can be based on known characteristics of a given type of cancer, and known sensitivity of the diagnostic technique—in the non-limiting example presented above, breast cancer might typically have first been detected as ductal carcinoma in situ, 0.5 cm. Still further steps include determining first probability of the cancer being present in a first set of one or more clinically significant remote sites based on the estimated initial characteristics; and determining second probability of the cancer being present in the first set of one or more clinically significant remote sites based on actual current characteristics of the given presenting cancer. These steps can be carried out, for example, using a nomogram such as the above-discussed MSK first nomogram, entering the actual cancer and demographic characteristics in the latter case, and the estimated characteristics in the former case. An even further step includes using the first and second probabilities to estimate incremental risk of incurring presence of the cancer at the first set of one or more clinically significant remote sites by delaying therapy for a unit time. For example, take the difference in probabilities and divide by half the time (in months) since the last (negative) diagnostic procedure (e.g., mammogram) to obtain the increased likelihood of sentinel node involvement from a one-month delay in treatment.

Furthermore regarding estimating initial characteristics of the given presenting cancer at the time when it would have first been detectable using the known diagnostic technique, most breast cancers start in the cells that line the ducts (ductal cancers), and microcalcifications are known to be of concern—see, e.g., American Cancer Society, Breast Cancer Prevention and Early Detection, Last Revised: Oct. 20, 2015, 2015 Copyright American Cancer Society, and American Cancer Society, Mammograms and Other Breast Imaging Tests, Last Revised: Apr. 25, 2016, 2014 Copyright American Cancer Society, both expressly incorporated herein by reference in their entirety for all purposes.

As used herein, a clinically significant remote site refers to any location in the body spaced away from the primary focus of cancer, wherein the presence of cancer at such site is clinically significant, such as for predicting survivability, need for certain kinds of treatment, and the like. Non-limiting examples include lymph nodes (sentinel or non-sentinel), distant metastases, etc.

A variety of uses can then be made of the estimated incremental risk. For example, in one aspect, a further step includes using known data regarding increased mortality risk associated with presence of cancer in the at least one clinically significant remote site, and the incremental risk of incurring presence of the cancer at the at least one clinically significant remote site by delaying therapy for a unit time, to obtain an estimate of incremental survivorship risk associated with the delaying of the therapy.

In another aspect, a further step includes using known data regarding increased harshness of a treatment regimen associated with presence of cancer in the at least one clinically significant remote site, and the incremental risk of incurring presence of the cancer at the at least one clinically significant remote site by delaying therapy for a unit time, to obtain an estimate of incremental risk for requiring a harsh treatment regimen associated with the delaying of the therapy.

In still another aspect, predictions are made for multiple subjects and used for triage when surgical or other treatment resources are limited. In this aspect, for example, the above-mentioned steps are carried out for a first subject, yielding incremental risk of incurring presence of the cancer at the at least one clinically significant remote site by delaying therapy for a unit time for the first subject, and further steps include estimating a time since a given presenting cancer of a second subject would have first been detectable using the known diagnostic technique; estimating initial characteristics of the given presenting cancer of the second subject at the time when it would have first been detectable using the known diagnostic technique; determining first probability of the cancer being present in a first set of one or more clinically significant remote sites of the second subject based on the estimated initial characteristics; determining second probability of the cancer being present in the first set of one or more clinically significant remote sites of the second subject based on actual current characteristics of the given presenting cancer; using the first and second probabilities for the second subject to estimate, for the second subject, incremental risk of incurring presence of the cancer at the first set of one or more clinically significant remote sites of the second subject by delaying therapy for a unit time; and using the incremental risks for the first and second subjects to carry out a triage.

In a further aspect, an additional step includes using known data regarding appropriate treatment dosage associated with presence of cancer in the at least one clinically significant remote site, and the incremental risk of incurring presence of the cancer at the at least one clinically significant remote site by delaying therapy for a unit time, to obtain a suggested treatment dosage for a subject.

In yet a further aspect, an additional step includes using known data regarding risk of an outcome associated with presence of cancer in the at least one clinically significant remote site, and the incremental risk of incurring presence of the cancer at the at least one clinically significant remote site by delaying therapy for a unit time, to obtain a hazard ratio for the outcome associated with the delaying of the therapy.

The uses that can be made of the estimated incremental risk are not exclusive; any one or more of the uses may be appropriate in a given case.

As noted above, more detailed estimate (e.g., using the second MSK nomogram in addition to the first) can be employed in some instances. Thus, in some cases, a further step includes determining a first conditional probability of the cancer being present in a secondary set of one or more clinically significant remote sites, given its presence in the first set of one or more clinically significant remote sites based on the estimated initial characteristics of the first detectable cancer. An even further step includes determining a second conditional probability of the cancer being present in the secondary set of one or more clinically significant remote sites, given its presence in the first set of one or more clinically significant remote sites based on the actual current characteristics of the given presenting cancer. Still further steps include using the first and second conditional probabilities to estimate incremental risk of incurring presence of the cancer at the second set of one or more clinically significant remote sites, given its presence in the first set of one or more clinically significant remote sites, by delaying therapy for a unit time; and combining the estimate of the incremental risk of incurring cancer at the first set of one or more clinically significant remote sites as a result of delaying therapy for a unit time with the estimate of the incremental risk (incremental addition to the conditional probability) of the cancer being present in the secondary set of one or more clinically significant remote sites, given its presence in the first set of one or more clinically significant remote sites, to obtain an estimate of the incremental risk of incurring cancer at the secondary set of one or more clinically significant remote sites. The aforementioned uses that can be made of the estimated incremental risk are applicable when estimating in this more detailed fashion, as well.

In a non-limiting exemplary application of this more detailed method, the cancer is breast cancer; the known diagnostic technique is mammography; the first set of one or more clinically significant remote sites includes a sentinel lymph node; and the second set of one or more clinically significant remote sites includes a non-sentinel lymph node.

In a non-limiting exemplary application of the simpler method, the cancer is breast cancer; the known diagnostic technique is mammography; and the first set of one or more clinically significant remote sites includes a sentinel lymph node.

Other types of risks can be predicted as appropriate; e.g., risk of incurring distant metastases.

In some cases, an exemplary system can be implemented using software performing calculations analogous to the MSK nomograms, showing risk in a user-selectable variety of ways, e.g. in terms of hazard ratio, increase in risk of death in 5 or 10 years, decrease in expected years of life, or decrease in quality-years of life. The system can also compare the impact of delaying therapy to the benefit of chemotherapy or immunotherapy and the associated costs. In other words, a month of delay in treatment can be thought of as undermining X % of the effect of chemo or immunotherapy, and at a total cost of Y, for, say immunotherapy, the expected dollar impact is $(X/100)Y.

Figure 8:
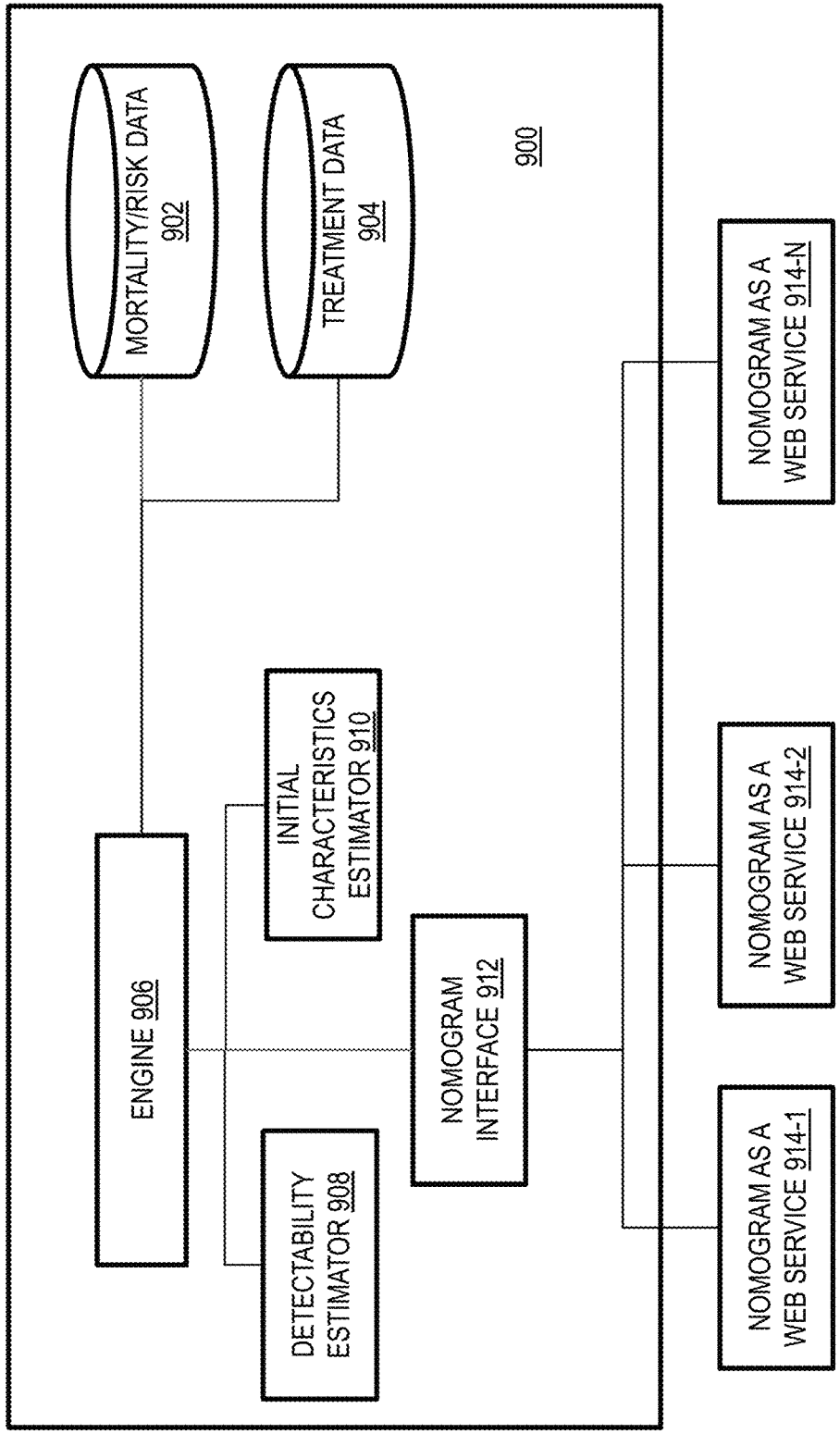
FIG. 8 is a system block diagram/software architecture diagram according to an embodiment of the present invention.

FIG. 8 shows an exemplary system 900 in accordance with an aspect of the invention. The components of system 900 may reside, for example, as a workload 96 in a workload layer of a cloud computing environment 90. Engine 906 interfaces with detectability estimator 908 which estimates when the given presenting cancer would first have been detectable using a known diagnostic technique such as mammography; it can be as simple as code which prompts a user for the time since the last diagnostic procedure (negative) and divides by two or can include more sophisticated rules instantiated in a rules engine or the like. Engine 906 interfaces with initial characteristics estimator 910 which estimates the initial characteristics of the presenting cancer at the time in the past when it could first have been discovered; it can be as simple as code which stores an estimate for a given type of cancer (e.g., DCIS of a certain size for breast cancer) or can include more sophisticated rules instantiated in a rules engine or the like. Nomogram interface 912 (e.g., an API such as a RESTFUL API or the like) allows the engine 902 to interface with one or more external nomograms 914-1, 914-2, . . . 914-N (collectively, 914). In a non-limiting example, the nomograms are made available to the engine 906 as web services. Alternatively, the user can access the nomograms separately or as part of a composite web page and the results of the nomograms are provided (e.g. manually) to the engine. Databases 902, 904 hold, respectively, mortality and risk data, and treatment data. Engine 906 employs a suitable user interface (omitted to avoid clutter) to obtain the actual current presenting and demographic characteristics; obtains the estimated time of first detectability and initial characteristics from estimators 908, 910; and interfaces with one or more external nomograms to obtain the first and second probabilities. It then calculates the incremental risk (e.g., using a simple model such as linear interpolation or a more sophistical model). The engine then accesses the databases 902 and/or 904 as needed to use the estimated incremental risk to obtain survivorship risk, increased risk for a harsh treatment regimen, triage, treatment dosage, hazard ratio, and the like. While architectures other than that shown in FIG. 8 can be employed, the architecture of FIG. 8 has the advantage of reducing the amount of data entry to increase computational efficiency and accuracy.

Figure 9:
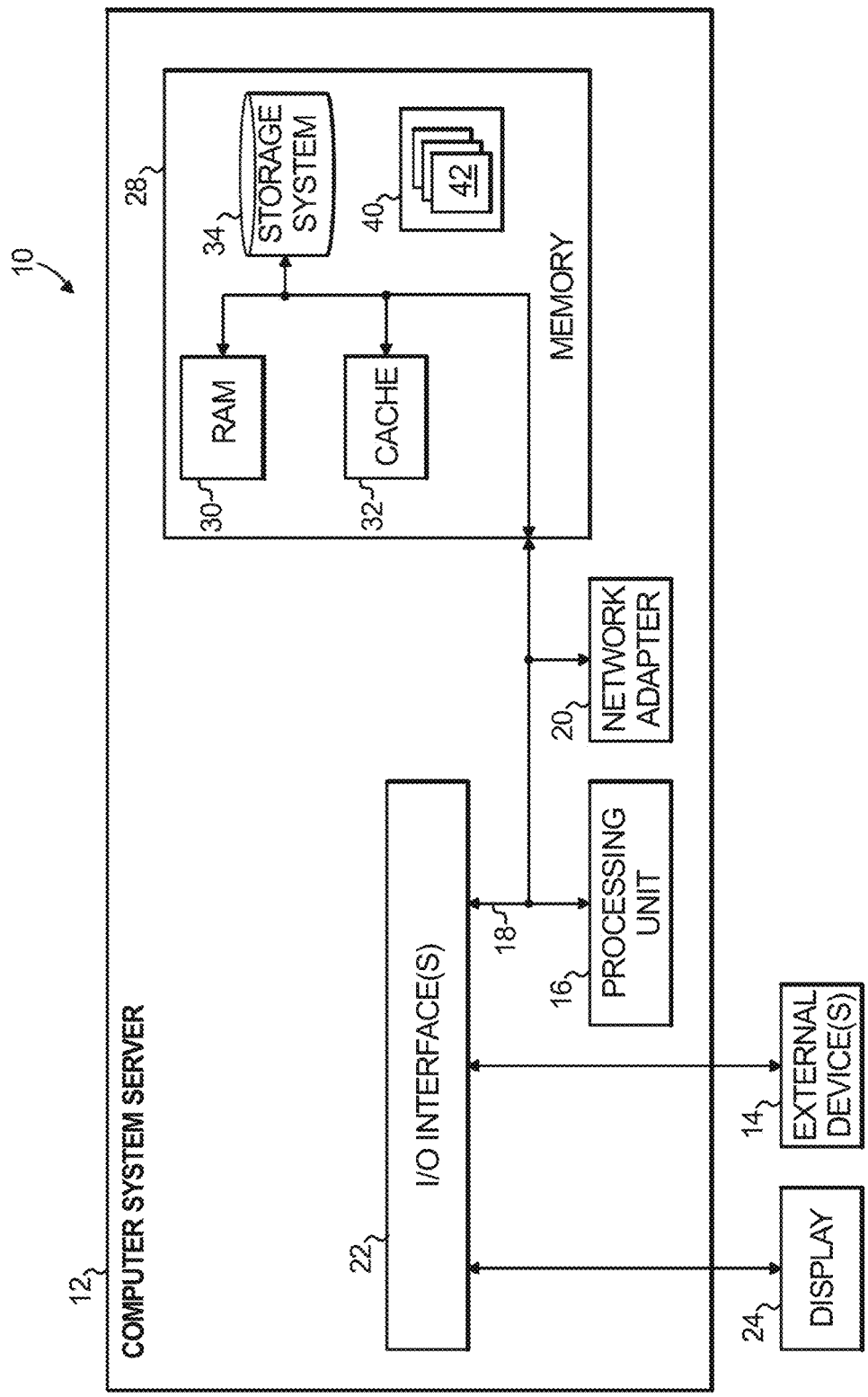
FIG. 9 depicts a computer system that may be useful in implementing one or more aspects and/or elements of the invention, also representative of a cloud computing node according to an embodiment of the present invention.

One or more embodiments of the invention, or elements thereof, can be implemented in the form of an apparatus including a memory and at least one processor that is coupled to the memory and operative to perform exemplary method steps. FIG. 9 depicts a computer system that may be useful in implementing one or more aspects and/or elements of the invention, also representative of a cloud computing node according to an embodiment of the present invention. Referring now to FIG. 9, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG., computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA)

bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 9, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 9) running a server program. It will be understood that such a physical server may or may not include a display and keyboard.

One or more embodiments can be at least partially implemented in the context of a cloud or virtual machine environment, although this is exemplary and non-limiting. Reference is made back to FIGS. 1-2 and accompanying text. Consider, e.g., database software 68 (implementing, e.g., 902, 904) accessed via a workload 96 for providing the various survival properties as discussed with respect to the embodiments, and more generally, the elements in FIG. 8.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules. For example, elements in FIG. 8 can be implemented as modules 42.

One example of user interface that could be employed in some cases is hypertext markup language (HTML) code served out by a server or the like, to a browser of a computing device of a user. The HTML is parsed by the browser on the user's computing device to create a graphical user interface (GUI).

Exemplary System and Article of Manufacture Details

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A non-transitory computer readable medium comprising computer executable instructions which when executed by a computer cause the computer to perform a method of treating cancer, the method comprising the steps of:
   estimating a time since a given presenting cancer would have first been detectable using a known diagnostic technique;
   estimating initial characteristics of said given presenting cancer at said time when it would have first been detectable using said known diagnostic technique;
   determining first probability of said cancer being present in a first set of one or more clinically significant remote sites based on said estimated initial characteristics;
   determining second probability of said cancer being present in said first set of one or more clinically significant remote sites based on actual current characteristics of said given presenting cancer;
   using said first and second probabilities to estimate incremental risk of incurring presence of said cancer at said first set of one or more clinically significant remote sites by delaying therapy for a unit time;
   providing said therapy to treat said given presenting cancer based at least in part on said incremental risk of incurring presence of said cancer at said at least one clinically significant remote site by delaying therapy for a unit time.

2. The non-transitory computer readable medium of claim 1, wherein said method steps further comprise:
   determining a first conditional probability of said cancer being present in a secondary set of one or more clinically significant remote sites, given its presence in said first set of one or more clinically significant remote sites based on the estimated initial characteristics of the first detectable cancer;
   determining a second conditional probability of said cancer being present in said secondary set of one or more clinically significant remote sites, given its presence in the first set of one or more clinically significant remote sites based on the actual current characteristics of said given presenting cancer;
   using said first and second conditional probabilities to estimate incremental risk of incurring presence of said cancer at said second set of one or more clinically significant remote sites, given its presence in the first set of one or more clinically significant remote sites, by delaying therapy for a unit time; and
   combining the estimate of the incremental risk of incurring cancer at said first set of one or more clinically significant remote sites as a result of delaying therapy for a unit time with the estimate of the incremental risk of said cancer being present in the secondary set of one or more clinically significant remote sites, given its presence in the first set of one or more clinically significant remote sites, to obtain an estimate of the incremental risk of incurring cancer at the secondary set of one or more clinically significant remote sites by delaying said therapy for said unit time.

3. An apparatus for treating cancer, comprising:
   a memory; and
   at least one processor, coupled to said memory, and operative to:
      estimate a time since a given presenting cancer would have first been detectable using a known diagnostic technique;
      estimate initial characteristics of said given presenting cancer at said time when it would have first been detectable using said known diagnostic technique;
      determine first probability of said cancer being present in a first set of one or more clinically significant remote sites based on said estimated initial characteristics;
      determine second probability of said cancer being present in said first set of one or more clinically significant remote sites based on actual current characteristics of said given presenting cancer;
      use said first and second probabilities to estimate incremental risk of incurring presence of said cancer at said first set of one or more clinically significant remote sites by delaying therapy for a unit time;
      providing said therapy to treat said given presenting cancer based at least in part on said incremental risk of incurring presence of said cancer at said at least one clinically significant remote site by delaying therapy for a unit time.

4. The apparatus of claim 3, wherein said at least one processor is further operative to:
   determine a first conditional probability of said cancer being present in a secondary set of one or more clinically significant remote sites, given its presence in said first set of one or more clinically significant remote sites based on the estimated initial characteristics of the first detectable cancer;
   determine a second conditional probability of said cancer being present in said secondary set of one or more clinically significant remote sites, given its presence in the first set of one or more clinically significant remote sites based on the actual current characteristics of said given presenting cancer;
   use said first and second conditional probabilities to estimate incremental risk of incurring presence of said cancer at said second set of one or more clinically significant remote sites, given its presence in the first set of one or more clinically significant remote sites, by delaying therapy for a unit time; and
   combine the estimate of the incremental risk of incurring cancer at said first set of one or more clinically significant remote sites as a result of delaying therapy for a unit time with the estimate of the incremental risk of said cancer being present in the secondary set of one or more clinically significant remote sites, given its presence in the first set of one or more clinically significant remote sites, to obtain an estimate of the incremental risk of incurring cancer at the secondary set of one or more clinically significant remote sites by delaying said therapy for said unit time.

5. The apparatus of claim 4, wherein:
said cancer comprises breast cancer;
said known diagnostic technique comprises mammography;
said first set of one or more clinically significant remote sites comprises a sentinel lymph node; and
said second set of one or more clinically significant remote sites comprises a non-sentinel lymph node.

6. The apparatus of claim 3, wherein:
said cancer comprises breast cancer;
said known diagnostic technique comprises mammography; and
said first set of one or more clinically significant remote sites comprises a sentinel lymph node.

7. The apparatus of claim 3, wherein said first and second probabilities are determined via nomogram and wherein said incremental risk is estimated via interpolation.

8. The non-transitory computer readable medium of claim 1, wherein said computer executable instructions comprise a plurality of distinct software modules, each of the distinct software modules being embodied on said non-transitory computer readable medium, and wherein the distinct software modules comprise a detectability estimator module, an initial characteristics estimator module, a coordinating engine module, and a nomogram interface module configured to interface with at least one external nomogram;
wherein:
said instructions cause said computer to estimate said time since said given presenting cancer would have first been detectable using a known diagnostic technique by executing, within a cloud computing environment, said detectability estimator module;
said instructions cause said computer to estimate said initial characteristics of said given presenting cancer at said time when it would have first been detectable using said known diagnostic technique by executing, within said cloud computing environment, said initial characteristics estimator module;
said instructions cause said computer to determine said first probability of said cancer being present in said first set of one or more clinically significant remote sites based on said estimated initial characteristics by executing said coordinating engine interfacing with said external nomogram as a web service, via said nomogram interface;
said instructions cause said computer to determine said second probability of said cancer being present in said first set of one or more clinically significant remote sites based on actual current characteristics of said given presenting cancer by executing said coordinating engine interfacing with said external nomogram as a web service, via said nomogram interface; and
said instructions cause said computer to use said first and second probabilities to estimate said incremental risk of incurring presence of said cancer at said first set of one or more clinically significant remote sites by delaying therapy for a unit time by executing said coordinating engine.

9. The apparatus of claim 3, further comprising a plurality of distinct software modules, each of the distinct software modules being embodied on a computer-readable storage medium, and wherein the distinct software modules comprise a detectability estimator module, an initial characteristics estimator module, a coordinating engine module, and a nomogram interface module configured to interface with at least one external nomogram;
wherein:
said at least one processor is operative to estimate said time since said given presenting cancer would have first been detectable using a known diagnostic technique by executing, within a cloud computing environment, said detectability estimator module;
said at least one processor is operative to estimate said initial characteristics of said given presenting cancer at said time when it would have first been detectable using said known diagnostic technique by executing, within said cloud computing environment, said initial characteristics estimator module;
said at least one processor is operative to determine said first probability of said cancer being present in said first set of one or more clinically significant remote sites based on said estimated initial characteristics by executing said coordinating engine interfacing with said external nomogram as a web service, via said nomogram interface;
said at least one processor is operative to determine said second probability of said cancer being present in said first set of one or more clinically significant remote sites based on actual current characteristics of said given presenting cancer by executing said coordinating engine interfacing with said external nomogram as a web service, via said nomogram interface; and
said at least one processor is operative to use said first and second probabilities to estimate said incremental risk of incurring presence of said cancer at said first set of one or more clinically significant remote sites by delaying therapy for a unit time by executing said coordinating engine.

10. The non-transitory computer readable medium of claim 1, said method further comprising using known data regarding appropriate treatment dosage associated with presence of cancer in said at least one clinically significant remote site, and said incremental risk of incurring presence of said cancer at said at least one clinically significant remote site by delaying therapy for a unit time, to obtain a suggested treatment dosage for a subject; and wherein said step of providing said therapy to treat said given presenting cancer based at least in part on said incremental risk of incurring presence of said cancer at said at least one clinically significant remote site by delaying therapy for a unit time comprises providing said therapy in accordance with the suggested treatment dosage.

11. The non-transitory computer readable medium of claim 1 wherein said step of providing said therapy to treat said given presenting cancer based at least in part on said incremental risk of incurring presence of said cancer at said at least one clinically significant remote site by delaying therapy for a unit time further comprises providing said therapy to treat said given presenting cancer either before or after said unit time based at least in part based at least in part on said incremental risk of incurring presence of said cancer at said at least one clinically significant remote site by delaying therapy for said unit time.

12. The non-transitory computer readable medium of claim 1 wherein said therapy to treat said given presenting cancer comprises at least one of surgery, chemotherapy, and radiation.

13. A non-transitory computer readable medium comprising computer executable instructions which when executed by a computer cause the computer to perform a method of treating cancer, the method comprising the steps of:
   estimating a time since a given presenting cancer of a first subject would have first been detectable using a known diagnostic technique;
   estimating initial characteristics of said given presenting cancer of said first subject at said time when it would have first been detectable using said known diagnostic technique;
   determining first probability of said cancer being present in a first set of one or more clinically significant remote sites of said first subject based on said estimated initial characteristics;
   determining second probability of said cancer being present in said first set of one or more clinically significant remote sites of said first subject based on actual current characteristics of said given presenting cancer;
   using said first and second probabilities for said first subject to estimate, for said first subject, incremental risk of incurring presence of said cancer at said first set of one or more clinically significant remote sites of said first subject by delaying therapy for a unit time for said first subject;
   estimating a time since a given presenting cancer of a second subject would have first been detectable using said known diagnostic technique;
   estimating initial characteristics of said given presenting cancer of said second subject at said time when it would have first been detectable using said known diagnostic technique;
   determining first probability of said cancer being present in a first set of one or more clinically significant remote sites of said second subject based on said estimated initial characteristics;
   determining second probability of said cancer being present in said first set of one or more clinically significant remote sites of said second subject based on actual current characteristics of said given presenting cancer;
   using said first and second probabilities for said second subject to estimate, for said second subject, incremental risk of incurring presence of said cancer at said first set of one or more clinically significant remote sites of said second subject by delaying therapy for said unit time; and
   providing said therapy to said first and second patients to treat said presenting cancers based at least in part on said incremental risks for said first and second subjects.

14. The computer-readable medium of claim 13, wherein an order in which said therapy is provided to said first and second patients is determined based at least in part on said incremental risks for said first and second subjects.

15. The computer-readable medium of claim 13, wherein said step of providing said therapy to said first and second patients to treat said presenting cancers based at least in part on said incremental risks for said first and second subjects further comprises providing said therapy to said first patient before providing said therapy to said second patient based at least in part on said incremental risks for said first and second subjects.

16. The computer-readable medium of claim 15, wherein said therapy is provided to said first patient before said therapy is provided to said second patient when said incremental risk for said first patient is greater than said incremental risk for said second subject, and wherein said therapy is provided to said second patient before said therapy is provided to said first patient when said incremental risk for said second patient is greater than said incremental risk for said first subject.

17. The computer-readable medium of claim 13, wherein said step of providing said therapy to said first and second patients to treat said presenting cancers based at least in part on said incremental risks for said first and second subjects further comprises:
   providing said therapy to said first subject either before or after said unit time based at least in part on said incremental risks for said first and second subject; and
   providing said therapy to said second subject either before or after said unit time based at least in part on said incremental risks for said first and second subject.

18. The computer-readable medium of claim 13, wherein said step of providing said therapy to said first and second patients to treat said presenting cancers based at least in part on said incremental risks for said first and second subjects further comprises, based at least in part on said incremental risks for said first and second subject, providing said therapy to said first subject before said unit time and providing said therapy to said second subject after said unit time.

19. The computer-readable medium of claim 13, wherein said step of providing said therapy to said first and second patients to treat said presenting cancers based at least in part on said incremental risks for said first and second subjects further comprises, when said incremental risk for said first subject is greater than said incremental risk for said second subject, providing said therapy to said first subject before said unit time and providing said therapy to said second subject after said unit time.

20. The computer-readable medium of claim 19, wherein said step of providing said therapy to said first and second patients to treat said presenting cancers based at least in part on said incremental risks for said first and second subjects further comprises, when said incremental risk for second subject is greater than said incremental risk for said first subject, providing said therapy to said second subject before said unit time and providing said therapy to said first subject after said unit time.

\* \* \* \* \*